US010993749B2

(12) United States Patent
Derouet et al.

(10) Patent No.: US 10,993,749 B2
(45) Date of Patent: May 4, 2021

(54) MEDICAL IMPLANT, AND KIT COMPRISING SUCH A MEDICAL IMPLANT AND A GRIPPER FOR SAID MEDICAL IMPLANT

(71) Applicant: NEOSTEO, Nantes (FR)

(72) Inventors: Guillaume Derouet, La Turballe (FR); Maxime Dechelette, Petit Mars (FR); Sylvain Sorin, La Bruffiere (FR)

(73) Assignee: NEOSTEO, Nantes (FR)

( * ) Notice: Subject to any disclaimer, the term of this patent is extended or adjusted under 35 U.S.C. 154(b) by 0 days.

(21) Appl. No.: 16/084,814

(22) PCT Filed: Mar. 15, 2017

(86) PCT No.: PCT/FR2017/050589
§ 371 (c)(1),
(2) Date: Sep. 13, 2018

(87) PCT Pub. No.: WO2017/158289
PCT Pub. Date: Sep. 21, 2017

(65) Prior Publication Data
US 2019/0069935 A1    Mar. 7, 2019

(30) Foreign Application Priority Data

Mar. 16, 2016  (FR) ...................................... 1652221

(51) Int. Cl.
*A61B 17/72*      (2006.01)
*A61B 17/88*      (2006.01)
(Continued)

(52) U.S. Cl.
CPC ...... *A61B 17/7258* (2013.01); *A61B 17/7291* (2013.01); *A61B 17/8872* (2013.01);
(Continued)

(58) Field of Classification Search
CPC ...... A61B 17/7258–7275; A61F 2/4225–4241
See application file for complete search history.

(56) References Cited

U.S. PATENT DOCUMENTS 6,200,330 B1 * 3/2001 Benderev ........... A61B 17/0401
411/358
9,168,074 B2 * 10/2015 Prandi .................... A61B 17/68
(Continued)

FOREIGN PATENT DOCUMENTS

FR        2 787 313        6/2000

OTHER PUBLICATIONS

International Search Report dated Dec. 19, 2016.

*Primary Examiner* — Nicholas J Plionis
*Assistant Examiner* — Steven J Cotroneo
(74) *Attorney, Agent, or Firm* — Ipsilon USA, LLP (57) ABSTRACT

A medical implant (1) designed to enable bony fusion between a first bone (20) and a second bone (21), said implant being in the form of an elongate part comprising, extending along the longitudinal axis of the part, a head (2) and a body (3) spaced apart from each other by a connection zone (4) connecting the head (2) to the body (3), said head (2) being suitable for being inserted into the first bone (20), said body (3) being suitable for being inserted into the second bone (21), said body (3) being a hollow body that is slotted longitudinally along at least a portion of its length in order to define at least three elastically deformable longitudinal tabs (5) by means of which said body (3) is suitable for being inserted into the second bone (21).

Each longitudinal tab (5) of the body (3) is an arcuate tab (5) that presents an outer face (6), i.e. directed towards the outside of the body (3), extending longitudinally in curved manner with curvature having its concave side directed towards the outside of the body (3).

16 Claims, 4 Drawing Sheets

(51) Int. Cl.
*A61B 90/00* (2016.01)
*A61F 2/28* (2006.01)
*A61F 2/30* (2006.01)
*A61F 2/42* (2006.01)
*A61B 17/56* (2006.01)
*A61B 17/68* (2006.01)

(52) U.S. Cl.
CPC ............... *A61B 90/03* (2016.02); *A61F 2/28* (2013.01); *A61B 2017/564* (2013.01); *A61B 2017/681* (2013.01); *A61B 2090/033* (2016.02); *A61F 2002/30161* (2013.01); *A61F 2002/30179* (2013.01); *A61F 2002/30303* (2013.01); *A61F 2002/4228* (2013.01)

(56) References Cited

U.S. PATENT DOCUMENTS

| | | | |
|---|---|---|---|
| 9,283,007 B2 * | 3/2016 | Augoyard | A61B 17/68 |
| 9,498,273 B2 * | 11/2016 | Thoren | A61B 17/8886 |
| 9,757,168 B2 * | 9/2017 | Seavey | A61B 17/7291 |
| 2003/0130660 A1 * | 7/2003 | Levy | A61B 17/746 606/63 |
| 2008/0132894 A1 * | 6/2008 | Coilard-Lavirotte | A61B 17/1604 606/60 |
| 2010/0131014 A1 * | 5/2010 | Peyrot | A61F 2/30 606/300 |
| 2011/0301652 A1 * | 12/2011 | Reed | A61B 17/7291 606/319 |
| 2011/0301653 A1 * | 12/2011 | Reed | A61B 17/1604 606/319 |
| 2014/0188237 A1 * | 7/2014 | McCormick | A61F 5/019 623/21.19 |
| 2015/0073413 A1 * | 3/2015 | Palmer | A61B 17/7266 606/63 |
| 2015/0141994 A1 * | 5/2015 | Cheney | B65B 63/02 606/63 |
| 2015/0320460 A1 * | 11/2015 | Taber | A61B 50/30 606/63 |

* cited by examiner

MEDICAL IMPLANT, AND KIT COMPRISING SUCH A MEDICAL IMPLANT AND A GRIPPER FOR SAID MEDICAL IMPLANT

RELATED APPLICATION

This application is a National Phase of PCT/FR2017/050589, filed on Mar. 15, 2017, which claims the benefit of priority from French Patent Application No. 16 52221, filed on Mar. 16, 2016, the entirety of which are incorporated by reference.

FIELD OF THE INVENTION

The invention relates to a medical implant and to a kit comprising such a medical implant and a gripper for said implant.

The invention relates more particularly to a medical implant designed to enable bony fusion between a first bone and a second bone, said implant being in the form of an elongate part comprising, extending along the longitudinal axis of the part, a head and a body spaced apart from each other by a connection zone connecting the head to the body, said head being suitable for being inserted into the first bone, the body being suitable for being inserted into the second bone, said body being a body that is slotted longitudinally along at least a portion of its length in order to define at least three elastically deformable longitudinal tabs by means of which said body is suitable for being inserted into the second bone.

PRIOR ART

A medical implant designed to enable two bones to be held in contact in abutment for the length of time required for bony fusion of the bones while they are held in contact is known from the prior art, as shown for example by European patent EP 2 544 633 and FR 2 913 876.

Such a medical implant is used in particular when performing interphalangeal arthrodesis, in particular of the fingers and toes, in order to surgically block the joint between two phalanges.

For a good result, it is necessary for the implant to adapt as well as possible to its environment and to be positioned in the most stable manner possible, in order to enable the bones to consolidate in the position selected by the surgeon.

Intra-medullary implants, such as those described in US document 2015/0141994, are not suitable since the body is not hollow and so bone regeneration cannot take place. Under such circumstances, this also means that its tabs ("legs") are not defined by longitudinal slots in the hollow body.

In addition, in document US 2015/0073413, the outer faces of the barbed tabs prevent easy insertion of the body of the implant into a bone.

OBJECT AND SUMMARY

An object of the invention is to provide a medical implant of the above-mentioned type, of a design that adapts well to its environment and that increases stability.

Another object of the invention is to provide a medical implant of the above-mentioned type, of a design that facilitates easy installation.

To this end, the invention provides a medical implant designed to enable bony fusion between a first bone and a second bone, said implant being in the form of an elongate part comprising, extending along the longitudinal axis of the part, a head and a body spaced apart from each other by a connection zone connecting the head to the body, said head being suitable for being inserted into the first bone, said body being suitable for being inserted into the second bone, said body being a body that is slotted longitudinally along at least a portion of its length in order to define at least three longitudinal tabs, with each longitudinal tab being separated from another longitudinal tab by a longitudinal slot, said longitudinal tabs by means of which said body is suitable for being inserted into the second bone being elastically deformable tabs, the implant being characterized in that each longitudinal tab of the body is an arcuate tab that presents an outer face, i.e. directed towards the outside of the body, extending longitudinally in curved manner with curvature having its concave side directed towards the outside of the body.

Making the body of the implant in the form of a hollow body serves to facilitate bone regeneration. Each longitudinal tab is separated from another longitudinal tab by a longitudinal slot. Each longitudinal tab is thus defined by longitudinal slots. Collectively, said longitudinal tabs define the circumferential structure of the body over said tabs. The longitudinal tabs are connected to the rest of the body at substantially a same position in the longitudinal direction. In other words, the tabs are not offset axially along said body. Thus, the free ends of the longitudinal tabs are arranged substantially in a common plane perpendicular to the longitudinal axis of the body and, in similar manner, the zones for connecting the tabs to the rest of the body are arranged in a common plane perpendicular to the longitudinal axis of the body, when the implant is in the non-stressed state.

The shape of the outer faces of the arcuate tabs adapts well to the medullary shaft. The tabs are suitable for adopting the shape of the internal profile of the medullary shaft and better resistance to tearing is obtained. By way of example, the flexibility and the shape of the tabs thus make it easier to pass through the constriction created by the cortices in the middle of the diaphysis of the bone.

In an embodiment, the implant is a flat head with two opposite faces that are mutually parallel or converging towards the top of the head. As a result the head is more compact.

In an embodiment, the implant is a head generally in the shape of a triangular arrowhead. This shape for the head can be impacted directly into the distal phalanx, without prior preparation. This facilitates installation.

In an embodiment, the sides of the triangle connecting the apex to the base of the triangle are notched like the notches in a Christmas tree shape. These notches ensure better retention of the implant in the bone.

In an embodiment, the head and the zone connecting the head to the body of the implant are hollowed out centrally in order to define an axial through passage inside the body. This central regeneration space between the tabs serves to improve primary stability and to improve the quality of natural osteogenesis, including on the axis of the medullary canal.

In an embodiment, at its zone connecting the head to the body, the implant includes at least two notches suitable for enabling the implant to be gripped by means of a gripper. The presence of these notches makes it possible to position the gripper perpendicularly to the longitudinal axis of the part constituting the implant. The gripper prevents backwards movement of the implant and forms a surface against which the distal phalanx can bear while it is being put into abutment.

In an embodiment, each notch is located at the base of a side of the triangle. The notches are thus circumferentially opposite one another, which facilitates taking hold of the implant.

In an embodiment, the outer faces of the tabs are provided, both at the free ends of the tabs and at the zone connecting the tabs to the rest of the body, with ribs or notches extending transversely to the longitudinal axis of the tabs. These ribs or notches increase the stability of the implant inside the bone.

In an embodiment, the free ends of the tabs have rounded tips. This facilitates inserting of the tabs into the bone.

In the embodiment, the arc formed by each arcuate tab between the free end of the tab and the zone connecting said tab to the rest of the body extends over at least 80% of the length of the tab.

In an embodiment, each arcuate tab presents, in its arcuate portion, a cross section that is substantially constant. The term "substantially constant" refers to a cross section that is constant to within ±10%.

In an embodiment each arcuate tab, in its arcuate portion, on going from the free end of the tab towards its zone connecting it to the rest of the body, extends towards the longitudinal axis of the body and then extends away from the longitudinal axis of said body, the transition zone between the zone in which the tab extends towards the axis and the zone in which the tab extends away from the axis being arranged between the free end of the tab and two thirds of the length of the tab taken from the free end of the tab, preferably between the first third and the second third of the length of the tab taken from the free end of the tab.

In an embodiment, with D1 corresponding to the diameter of the smallest circle inside which the outer faces of the tabs can be inscribed, D2 corresponding to the diameter of the smallest circle inside which the inner faces of the tabs can be inscribed, and D3 corresponding to the minimum distance between two adjacent tabs:

$D2 \geq (D1-D2)/2$ and, preferably, $D3 \geq (D1-D2)/2$.

The invention also provides a kit of the type including a medical implant designed to enable bony fusion between a first bone and a second bone, and a gripper, said implant being in the form of an elongate part comprising, extending along the longitudinal axis of the part, a head and a body spaced apart from each other by a connection zone connecting the head to the body, said head being suitable for being inserted into the first bone, said body being suitable for being inserted into the second bone, said body being a hollow body that is slotted longitudinally along at least a portion of its length in order to define at least three longitudinal tabs with each longitudinal tab being separated from another longitudinal tab by a longitudinal slot, said longitudinal tabs by means of which said body is suitable for being inserted into the second bone being elastically deformable tabs, the medical implant being characterized in that the medical implant is of the above-mentioned type.

The invention also provides a method of putting into place a medical implant designed to enable bony fusion between a first bone and a second bone, using a gripper, said implant being in the form of an elongate part comprising, extending along the longitudinal axis of the part, a head and a body spaced apart from each other by a connection zone connecting the head to the body, said body being a hollow body that is slotted longitudinally along at least a portion of its length in order to define at least three longitudinal tabs with each longitudinal tab being separated from another longitudinal tab by a longitudinal slot, said longitudinal tabs by means of which said body is suitable for being inserted into the second bone being elastically deformable tabs; the method being characterized in that, with the implant being gripped by the gripper at its connection zone, and with each longitudinal tab being an arcuate tab presenting an outer face, i.e. directed towards the outside of the body extending longitudinally in curved manner, with curvature having its concave side directed towards the outside of the body, the method comprises a step of inserting the body of the implant into a bone, referred to as the second bone such as a proximal phalanx, by using the gripper, until the gripper is positioned against the end of said bone, a step of inserting the head of the implant into a bone, referred to as the first bone, by abutting said first bone against the second bone, until the first bone is positioned to bear against the gripper, a step of removing the gripper, and a step of terminating abutment so as to fill in the space that was occupied by the gripper.

BRIEF DESCRIPTION OF THE FIGURES

The invention can be better understood on reading the following description of embodiments given with reference to the accompanying drawings, in which.

Figure 1:
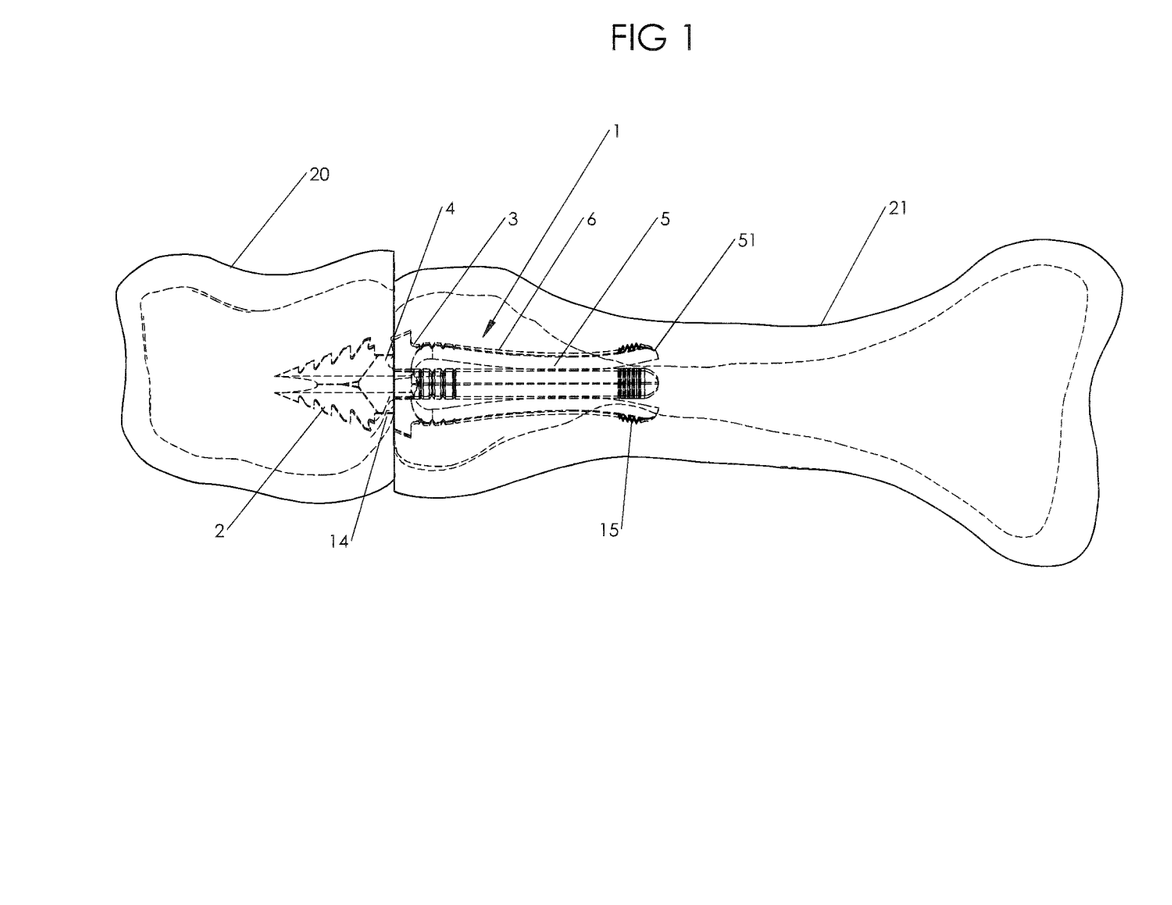
FIG. 1 is a transparent view of a first bone and a second bone having a medical implant in accordance with the invention mounted therein.
Figure 2:
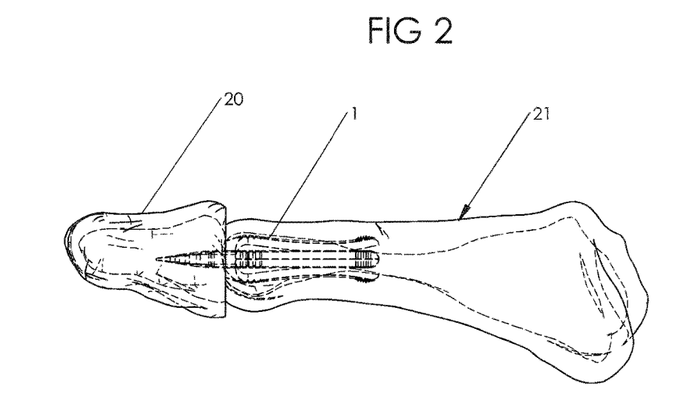
FIG. 2 is a transparent view, taken from another angle, of first and second bones with a medical implant in accordance with the invention in the mounted state.
Figure 3:
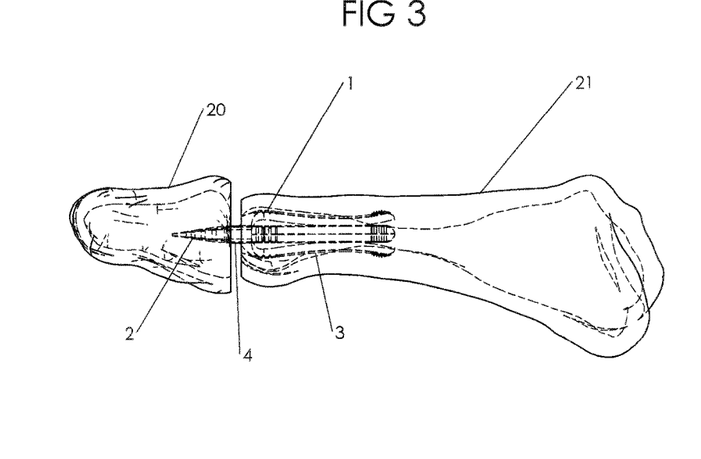
FIG. 3 is a transparent view of first and second bones with a medical implant in accordance with the invention in the mounted state, putting into abutment being in the process of completion, the gripper having just been removed.

As mentioned above, the invention provides a medical implant 1 designed to enable bony fusion between a first bone 20 formed in this example by a distal phalanx, and a second bone 21 formed by a proximal phalanx. In this example, the implant 1 is therefore designed to enable interphalangeal arthrodesis to be performed.

This implant 1 is in the form of an elongate part made in one piece. By way of example, this implant may be made by molding, by injection, or indeed by machining. The material suitable for making such an implant 1 may be any material that is biocompatible, optionally a metal. By way of example, the material may be titanium.

Figure 4:
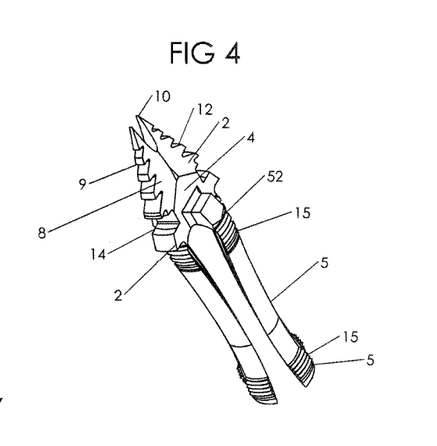
FIG. 4 is a perspective view of a medical implant in accordance with the invention.
Figure 5:
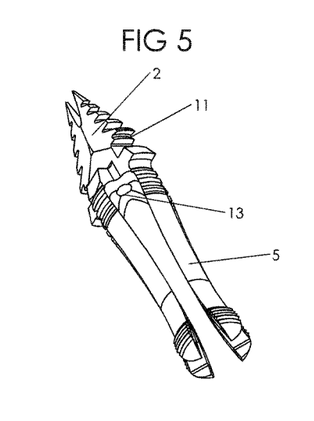
FIG. 5 is a perspective view, taken from another angle, of a medical implant in accordance with the invention.

Extending along a longitudinal axis of the part, this implant 1 comprises a head 2 and a body 3 spaced apart from each other by a connection zone 4 connecting the head 2 to the body 3.

The head 2 is designed to be inserted into the first bone 20, while the body 2 is designed to be inserted into the second bone 21. Naturally, the opposite solution could be envisaged, but it is not preferred.

The body 3 is a hollow body slotted longitudinally along a portion of its length in order to define four longitudinal tabs 5 in this example. Each longitudinal tab is separated from another longitudinal tab by a longitudinal slot. Each longitudinal tab is thus defined by longitudinal slots. Collectively, said longitudinal tabs define the circumferential structure of the body over said tabs. The longitudinal tabs are connected to the rest of the body at substantially a same position in the longitudinal direction. In other words, the tabs are not offset axially along said body. Thus, the free ends of the longitudinal tabs are arranged substantially in a common plane perpendicular to the longitudinal axis of the body and, in similar manner, the zones for connecting the tabs to the rest of the body are arranged in a common plane perpendicular to the longitudinal axis of the body. The number of longitudinal slots in the body is equal to the number of longitudinal tabs 5 of the body 3. These longitudinal tabs 5 are arcuate, i.e. generally in the shape of an arc. In particular, each of these longitudinal tabs 5 presents an outer face 6, i.e. a face directed towards the outside of the body 3, which face extends longitudinally in curved manner, with curvature having its concave side directed towards the outside of the body 3. This curvature follows a circularly arcuate curved line as contrasted with a succession of broken-line segments.

Each elastically-deformable longitudinal tab 5 also presents an inner face 7, i.e. a face directed towards the inside of the body and opposite from the outer face 6, also extending longitudinally in curved manner, with its convex side directed towards the inside of the body. This results in the curved longitudinal tabs 5 being thin, which serves to facilitate inserting them into the bone, without affecting their stability inside the bone.

In its arcuate portion, each arcuate tab 5 presents a cross section that is substantially constant. Thus, each arcuate tab 5 presents a cross section that is substantially constant over at least 80% of its length. The arc formed by each arcuate tab 5 between the free end 51 of the tab 5 and the zone 52 for connecting said tab 5 to the rest of the body 3 extends over at least 80% of the length of the tab 5. Thus, each arcuate tab 5, in its arcuate portion, on going from the free end 51 of the tab 5 towards its zone 52 connecting it to the rest of the body 3, extends towards the longitudinal axis of the body 3 and then extends away from the longitudinal axis of said body 3, the transition zone between the zone in which the tab extends towards the axis and the zone in which the tab extends away from the axis being arranged between the free end 51 of the tab 5 and two thirds of the length of the tab taken from the free end 51 of the tab 5, preferably between the first third and the second third of the length of the tab 5 taken from the free end 51 of the tab 5.

Figure 7:
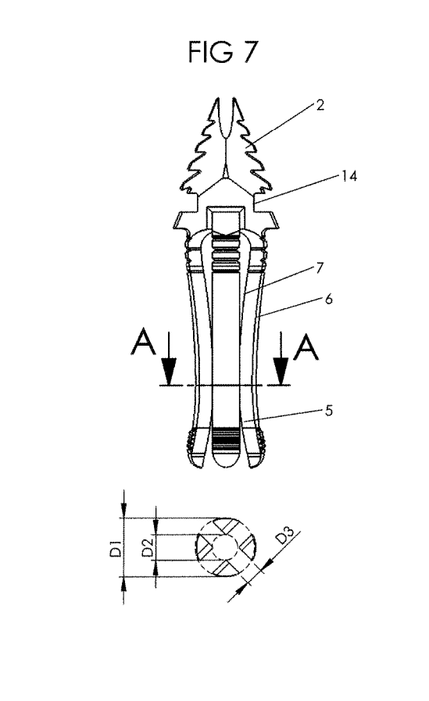
FIG. 7 is a perspective view of a medical implant in accordance with the invention, associated with a view of said implant in section on AA.

In the example shown in FIG. 7, with D1 corresponding to the diameter of the smallest circle inside which the outer faces 6 of the tabs can be inscribed, D2 corresponding to the diameter of the smallest circle inside which the inner faces 7 of the tabs can be inscribed, and D3 corresponding to the minimum distance between two adjacent tabs (5):

$D2 \geq (D1-D2)/2$ and, preferably, $D3 \geq (D1-D2)/2$.

The outer faces 6 of the tabs 5 are provided, both at the free ends 51 of the tabs 5 and at the zones 52 connecting the tabs 5 to the rest of the body 3, with ribs 15 or notches extending transversely to the longitudinal axis of the tabs 5. In this example, these ribs are ribs that are mutually parallel and substantially perpendicular to the longitudinal axis of the part.

The free ends of the tabs have rounded tips. Once again, this arrangement serves to facilitate inserting the tabs into the bone associated therewith.

Figure 6:
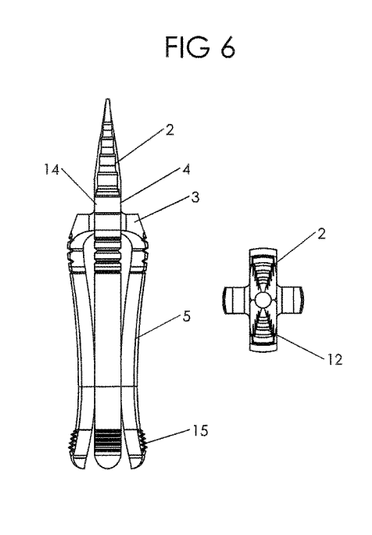
FIG. 6 is a perspective view, taken from another angle, of a medical implant in accordance with the invention and a front view taken from the tip end of the head of the implant.

The head 2 of the implant 1 is a head generally in the shape of a triangular arrowhead. This head is a flat head with the two opposite faces 8 of the triangle made to converge towards the apex of the triangle that forms the tip of the head. Each face 8 is a polyhedral face in the shape of a diamond tip, a V-shape, or similar. In equivalent manner, this face 8 could be made to be plane.

The sides 9 of the triangle connecting the apex 10 to the base 11 of the triangle are notched like the notches 12 in a Christmas tree shape. The edges of the sides of the triangle for connection to the faces 8 of the triangle are beveled. Once again, these edges could be straight.

This arrowhead shape of the head enables the head to be implanted directly into the first bone, without prior preparation of the bone.

Figure 8:
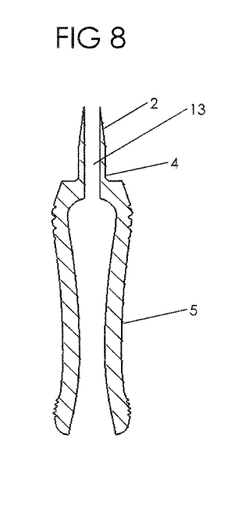
FIG. 8 is a longitudinal section view of a medical implant in accordance with the invention.

In order to improve the kit and in particular to enable it to pass a canula or to facilitate osteogenesis, in the central portion of the implant, the head 2, and the zone 4 connecting the head 2 to the body 3 of the implant are hollowed out centrally. This central hollow forms an axial through passage 13, opening out inside the body 3.

Figure 9:
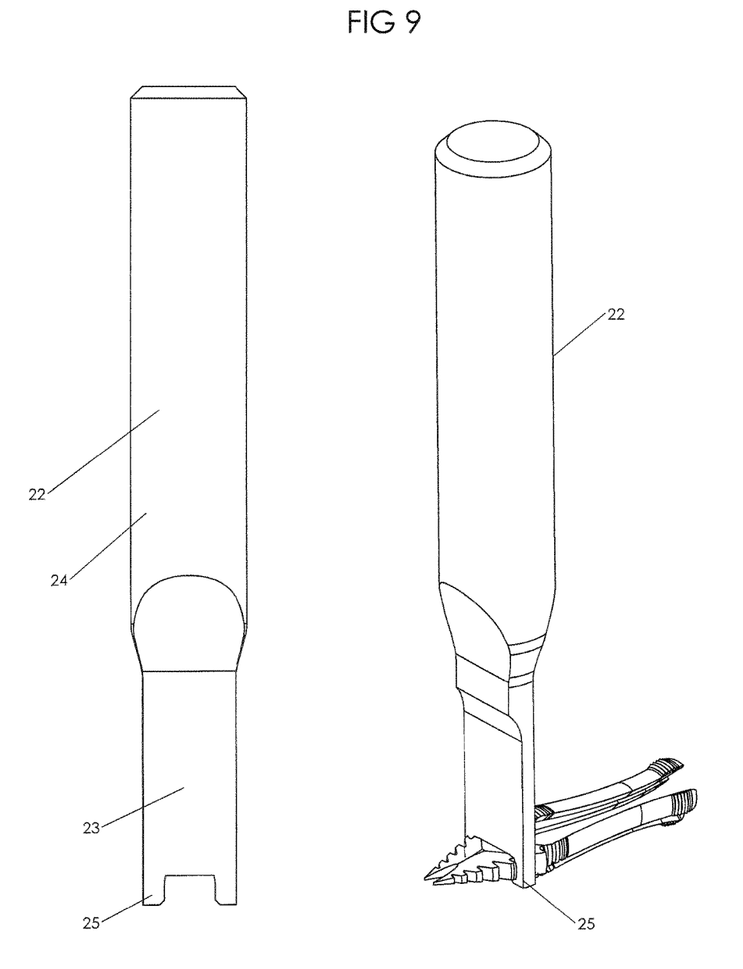
FIG. 9 is a view of the gripper alone and a view of the gripper when engaged on an implant.

At its zone 4 connecting the head 2 to the body 3, the implant 1 further includes at least two notches 14 suitable for enabling the implant 1 to be gripped by means of a gripper 22. Each notch 14 is located at the base of a side 9 of the triangle. These notches are therefore arranged opposite each other, and they are obtained by narrowing the cross section of the connection zone relative to the head and to the body.

In the space left free on the periphery of the part between two notches, the body may present point projections that co-operate with a flank of each notch closest to the body to form a bearing surface that is substantially plane, to perform a role that is described below.

Such an implant presents a length that generally lies in the range 10 millimeters (mm) to 30 mm. The length of the head of the implant represents at least 20% and at most half of the length of the total length of the implant.

In order to put such an implant into place, it is strongly recommended to use a gripper 22 of the type shown in FIG. 9. The gripper 22 comprises a handle 24, and a blade 23 arranged extending the handle, with the end of this blade 23 being shaped to form two teeth 25 arranged facing each other in the plane of the blade. Each tooth is designed to be inserted in a respective notch of the implant.

Thus, in the position for gripping the implant using the gripper, the plane of the blade of the gripper extends substantially perpendicularly to the longitudinal axis of the part. The implant gripped in this way by means of the gripper can be handled by the surgeon. The surgeon inserts the body of the implant into the medullary cavity of the second bone, in this example formed by a proximal phalanx. Insertion of the implant is facilitated by the design of the longitudinal tabs, which are inserted by their free ends into the medullary cavity of the bone.

Insertion continues until the blade of the gripper comes, via one of its faces referred to as its "first" face, to bear against the end of the second bone that is to be put into abutment with a bone referred to as the "first" bone.

The second phalanx, referred to as the "distal" phalanx, is engaged on the head of the implant. During this engagement, the gripper remains in place on the implant, in such a manner as to remain engaged until the end of the first bone comes into abutment against the second face of the blade of the gripper opposite from its first face.

The blade of the gripper is thus sandwiched between the abutting ends of the bones, which thus find themselves spaced apart from each other by a distance corresponding to the thickness of the blade, i.e. generally a thickness of less than 2 mm.

At this stage, the gripper may be removed by a movement in translation orthogonal to the axis of the medullary canal or to the longitudinal axis of the implant, and the first and second bones may be put into contact by the surgeon. During this final putting into abutment, the potential backwards movement of the implant inside at least one of the bones is equal to the thickness of the gripper, i.e. less than 2 mm, which has no effect on the stability of the implant, which is generally not the case in the state of the art, where backwards movement of the implant into the medullary canal is observed during abutment.

The connection zone of the implant is thus to be found at the arthrodesis line. The gripper may be pre-mounted on the medical implant, or it may be supplied separately.

The invention claimed is:

1. A medical implant enabling bony fusion between a first bone and a second bone, said implant comprising an elongate part, extending along a longitudinal axis of the part,
    a head and a body spaced apart from each other by a connection zone connecting the head to the body, said head being suitable for being inserted into the first bone,
    said body being suitable for being inserted into the second bone,
    said body being a hollow body that is slotted longitudinally along at least a portion of its length in order to define at least three longitudinal tabs with each longitudinal tab being separated from another longitudinal tab by a longitudinal slot, said longitudinal tabs by means of which said body is suitable for being inserted into the second bone being elastically deformable tabs;
    wherein each longitudinal tab of the body is an arcuate tab that presents an outer face directed towards the outside of the body, extending longitudinally in continuously curved manner with curvature having a continuously concave side directed towards the outside of the body,
    wherein each arcuate tab is arcuate from the free end of the tab towards its connection zone connecting it to the rest of the body, the curvature extends towards the longitudinal axis of the body and then extends away from the longitudinal axis of said body to form a transition zone between the zone in which the tab extends towards the axis and the zone in which the tab extends away from the axis, the transition zone arranged between the free end of the tab and two thirds of the length of the tab taken from the free end of the tab.

2. A medical implant according to claim 1, wherein the head of the implant is a flat head with two opposite faces that are mutually parallel or converging towards the top of the head.

3. A medical implant according to claim 1, wherein the head of the implant is in the shape of a triangular arrowhead.

4. A medical implant according to claim 3, wherein the sides of the triangle connecting the apex to the base of the triangle are notched like the notches in a Christmas tree shape.

5. A medical implant according to claim 4, wherein, at the connection zone connecting the head to the body, the implant includes at least two notches suitable for enabling the implant to be gripped by means of a gripper.

6. A medical implant according to claim 5, wherein each notch is located at the base of a side of said head of the implant in the shape of a triangular arrowhead.

7. A medical implant according to claim 1, the head and the zone connecting the head to the body of the implant are hollowed out centrally in order to define an axial through passage inside the body.

8. A medical implant according to claim 1, wherein the outer faces of the tabs are provided, both at the free ends of the tabs and at the connection zone connecting the tabs to the rest of the body, with ribs or notches extending transversely to the longitudinal axis of the tabs.

9. A medical implant according to claim 1, wherein the free ends of the tabs have rounded tips.

10. A medical implant according to claim 1, wherein an arc formed by each arcuate tab between the free end of the tab and the connection zone connecting said tab to the rest of the body extends over at least 80% of the length of the tab.

11. A medical implant according to claim 1, wherein each arcuate tab presents, in its arcuate portion, a cross section that is substantially constant.

12. A medical implant according to claim 1, wherein the transition zone between the zone in which the tab extends towards the axis and the zone in which the tab extends away from the axis is arranged between the first third and the second third of the length of the tab taken from the free end of the tab.

13. A medical implant according to claim 1, wherein with D1 corresponding to the diameter of the smallest circle inside which the outer faces of the tabs can be inscribed, D2 corresponding to the diameter of the smallest circle inside which the inner faces of the tabs can be inscribed, and D3 corresponding to the minimum distance between two adjacent tabs;

$$D2 \geq (D1-D2)/2.$$

14. A medical implant according to claim 1, wherein with D1 corresponding to the diameter of the smallest circle inside which the outer faces of the tabs can be inscribed, D2 corresponding to the diameter of the smallest circle inside which the inner faces of the tabs can be inscribed, and D3 corresponding to the minimum distance between two adjacent tabs;

$$D3 \geq (D1-D2)/2.$$

15. A bony fusion kit for bony fusion between a first bone and a second bone, said kit comprising;
    a medical implant having an elongate part, extending along a longitudinal axis of the part,
    a head and a body spaced apart from each other by a connection zone connecting the head to the body, said head being suitable for being inserted into the first bone,
    said body being suitable for being inserted into the second bone,
    said body being a hollow body that is slotted longitudinally along at least a portion of its length in order to define at least three longitudinal tabs with each longitudinal tab being separated from another longitudinal tab by a longitudinal slot, said longitudinal tabs by means of which said body is suitable for being inserted into the second bone being elastically deformable tabs; wherein each longitudinal tab of the body is an arcuate tab that presents an outer face directed towards the outside of the body, extending longitudinally in continuously curved manner with curvature having a continuously concave side directed towards the outside of the body, wherein each arcuate tab is arcuate from the free end of the tab towards its connection zone connecting it to the rest of the body, the curvature extends towards the longitudinal axis of the body and then extends away from the longitudinal axis of said body to form a transition zone between the zone in which the tab extends towards the axis and the zone in which the tab extends away from the axis, the transition zone arranged between the free end of the tab and two thirds of the length of the tab taken from the free end of the tab;

and a gripper.

16. A method of putting into place a medical implant enabling bony fusion between a first bone and a second bone, using a gripper, said implant being an elongate part comprising, extending along a longitudinal axis of the part, a head and a body spaced apart from each other by a connection zone connecting the head to the body, said body being a hollow body that is slotted longitudinally along at least a portion of its length in order to define at least three longitudinal tabs with each longitudinal tab being separated from another longitudinal tab by a longitudinal slot, said longitudinal tabs by means of which said body is suitable for being inserted into the second bone being elastically deformable tabs; the method being characterized in that, the implant being gripped by the gripper at its connection zone, and with each longitudinal tab being an arcuate tab presenting an outer face directed towards the outside of the body extending longitudinally in continuously curved manner, with curvature having a continuously concave side directed towards the outside of the body, the method comprises a step of inserting the body of the implant into a bone, referred to as the second bone, by using the gripper, until the gripper is positioned against the end of said bone, a step of inserting the head of the implant into a bone, referred to as the first bone, by abutting said first bone against the second bone, until the first bone is positioned to bear against the gripper, a step of removing the gripper, and a step of terminating abutment so as to fill in the space that was occupied by the gripper.

* * * * *